US00PP09372P

United States Patent [19]

Iverson

[11] Patent Number: Plant 9,372

[45] Date of Patent: Nov. 14, 1995

[54] DAYLILY PLANT NAMED 'YELLOW SILK RUFFLES'

[76] Inventor: Ronald C. Iverson, Rte. 1, Box 326B, Orange, Va. 22960

[21] Appl. No.: 355,296

[22] Filed: Dec. 12, 1994

[51] Int. Cl.[6] ..... A01H 5/00

[52] U.S. Cl. ..... Plt./87.4

[58] Field of Search ..... Plt./87.4

[56] References Cited

U.S. PATENT DOCUMENTS

P.P. 7,357 10/1990 Kirchoff ..... Plt./87.4

P.P. 8,140 2/1993 Apps et al. ..... Plt./87.4

*Primary Examiner*—James R. Feyrer

*Attorney, Agent, or Firm*—Foley & Lardner

[57] ABSTRACT

An new cultivar of dalylily plant named Yellow Silk Ruffles, characterized by its very large light yellow-orange flowers with very ruffled petal edges, very fragrant flowers which are fade resistant, reblooming ability, vigorous growth habit, and its very floriferous.

2 Drawing Sheets

The present invention comprises a new and distinct cultivar of daylily which belongs to the genus Hemerocallis, and is hereinafter referred to by the cultivar name Yellow Silk Ruffles.

The new cultivar is the result of an open pollination breeding program in which numerous unnamed and unidentified daylily cultivars were planted in an open cultivated field in a controlled environment in Merriville, Ind. Seed was collected from the open polliated female plants and grown in a controlled area in Merriville, Ind.

Well over one thousand seedling plants were mass-selected in early summer 1990, and grown out in Long Grove, Ill. in a cultivated area. The new cultivar was discovered and selected from the mass-selected plants by inventor Ronald C. Inverson in August 1980 in such area in Long Grove, Ill.

The first act of asexual reproduction of Yellow Silk Ruffles was accomplished when divisions were taken from the selection in September 1990 in a controlled environmental in Long Grove, Ill. by Ronald C. Iverson. Horticulture examination of selected units initiated in June 1991 has demonstrated that the combination of characteristics as herein disclosed for Yellow Silk Ruffles are firmly fixed and are retained through successive generations of asexual reproduction.

Yellow Silk Ruffles has not been observed under all possible environmental conditions. The phenotype may vary significantly with variations in environment such as temperature, light intensity, and daylength without, however, any variance in genotype. The following observations, measurements, and comparisons describe plants grown in Long Grove, Ill. under greenhouse conditions which approximate those generally used in commerical practice.

The following traits have been repeatedly observed and are determined to be basic characteristics of Yellow Silk Ruffles which in combination distinguish this daylily as a new and distinct cultivar.

1. Light yellow-orange flower color, with the edges of the petals being ruffled and deeply crimped. The flowers are sun resistant and do not fade in bright light.

2. Flowers are highly fragrant.

3. Individual flowers are very large, being approximately 5¾ inches in diameter.

4. The plant has a healthy and vigorous growth habit.

5. Individual fans produce 2–3 flowering scapes in each season. This ability to rebloom is a significant feature of the new cultivar.

6. Bloom season in Illinois is from late June continuously until October. Flower opens about 7:00 a.m. and remains open the entire day.

The new cultivar is similar in certain respects to Fragrant Treasure, disclosed in U.S. Plant Pat. No. 8,140, and also characterized by fragrant flowers, reblooming habit and yellow flowers. Yellow Silk ruffles in distinguished from Fragrant Treasure by its larger flowers, slightly darker yellow petal color, and its prominent midveins which are darker yellow in color compared to the surrounding petal area.

The accompanying color photographic drawings show typical flower characteristics of Yellow Silk Ruffles, with colors being as true as possible with illustrations of this type.

The photo on sheet 1 is a side view of typical plants of the new cultivar grown in an open field.

The photo on sheet 2 is a greatly enlarged top view showing in much greater detail the flower parts.

In the following description, color references are made to The Royal Horticultural Society Colour Chart. The color values were determined between 11:30 a.m. to 12:30 p.m. on June 30 under hazy light conditions at Long Grove, Ill.

Parentage:

*Origin.*—Selection from mass-selected seedling population obtained by open pollination.

*Parentage.*—Seed parent: Unknown. Pollen parent: Unknown.

Classification:

*Botanic.*—Hemerocallis hybrid.

*Commercial.*—Large flower daylily cv. Yellow Silk Ruffles.

Plant description:

*Form.*—Wide, spreading.

*Height.*—Approximately 24 inches.

*Growth habit.*—Clump forming, vigorous.

*Strength.*—Moderate.

*Foliage.*—Size of leaf: 1½ inches wide by 20 inches long. Shape of leaf: Typical Hemerocallis. Texture: Fine. Color: Green 144A.

*Bulbs.*—Size: 6 inches long. Color: Tan.

Bud description:

*Form.*—Column shaped.

*Size.*—3 inches long.

*Opening.*—Flat.

*Color.*—Green.

Flowering description:

*Blooming habit.*—Late June continuously until October.

*Size.*—Very large, 5¾ inches in diameter.

*Borne.*—Perpendicular to flowering scape.

*Shape.*—Star.

*Tepalage.*—Number of tepals: 6. Arrangement: Star. Color: Upper surface: 16D. Under surface: 14C. Tepal longevity: One day. Spotting: No markings. Color change: Color is very persistent with no or very little fading even on hot days. Texture: Thick, deeply ruffled edges, edges are crimped and thinner. Veins are depressed and 17A in color. Midveins are particularly prominent. Disease resistance: No recognized problems. Fragrance: Slightly sweet fragrance. Lasting quality; One day.

Reproductive organs:

*Stamens, anthers.*—Arrangement: Central, erect. Length: 2 inches. Number: Six. Filaments: Six.

*Pistils.*—3 inches in length.

*Stigma.*—Light yellow.

Fruit:

*Shape.*—Round.

*Color at maturity.*—Black.

I claim:

1. A new and distinct cultivar of daylily plant named Yellow Silk Ruffles, as illustrated and described.

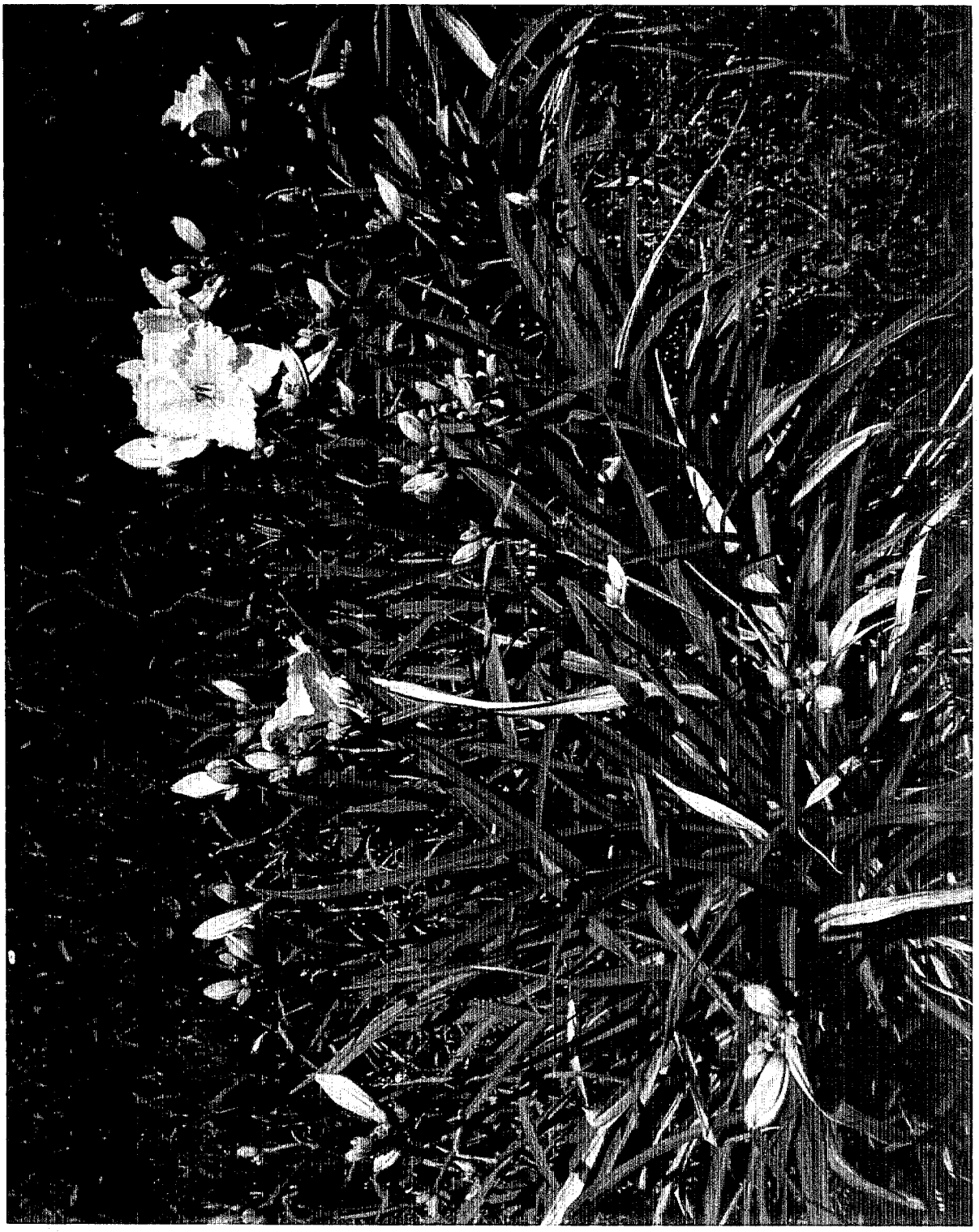

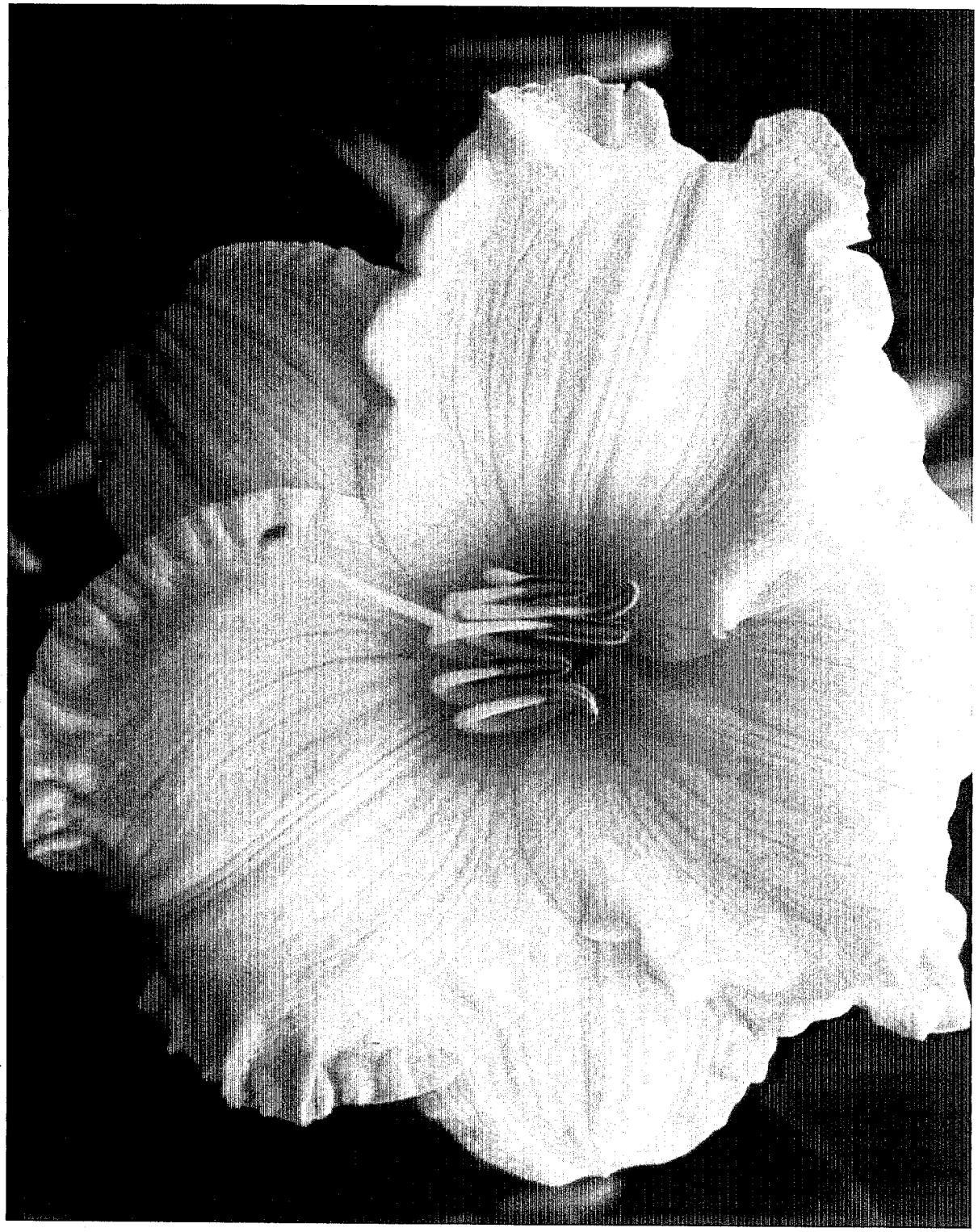

* * * * *